United States Patent [19]
Chatterjee et al.

[11] Patent Number: 4,571,407
[45] Date of Patent: Feb. 18, 1986

[54] PHARMACEUTICAL COMPOSITIONS CONTAINING BILOBALID FOR THE TREATMENT OF NEUROPATHIES

[75] Inventors: Shyam S. Chatterjee; Bernard L. Gabard, both of Karlsruhe; Hermann E. W. Jaggy, Bad Schönborn, all of Fed. Rep. of Germany

[73] Assignee: Dr. Willmar Schwabe GmbH & Co., Karlsruhe, Fed. Rep. of Germany

[21] Appl. No.: 662,598

[22] Filed: Oct. 19, 1984

[30] Foreign Application Priority Data

Oct. 27, 1983 [DE] Fed. Rep. of Germany ....... 3338995

[51] Int. Cl.$^4$ ............................................ A61K 31/36
[52] U.S. Cl. .................................................... 514/464
[58] Field of Search ......................... 424/279; 514/464

[56] References Cited
PUBLICATIONS

R. T. Major, Science, 157, 1270–1273 (1967).
Weinges and Bahr, Liebigs Ann–Chem, 724, 214–216 (1969).
Nakanishi, Major, Weinges et al., J. Am. Chem. Soc., 94, 3544–3546 (1971).
Chatterjee and Trunzler, Artezeitschrift fus Naturheilverfahren, 22, 593–604 (1981).

Primary Examiner—Stanley J. Friedman
Attorney, Agent, or Firm—Kenyon & Kenyon

[57] ABSTRACT

Medicaments containing bilobalid which can be used to control nervous diseases are described.

4 Claims, 2 Drawing Figures

PHARMACEUTICAL COMPOSITIONS CONTAINING BILOBALID FOR THE TREATMENT OF NEUROPATHIES

BACKGROUND OF THE INVENTION

The isolation of a lactone compound having the molecular formula $C_{15}H_{18}O_8$ from the leaves of *Ginkgo biloba* was first mentioned in 1967 by R. T. Major (Science 157 (1967), 1270 to 1273). The physicochemical properties of this compound and derivatives were described, and the name bilobalid was proposed, by K. Weinges and W. Bähr (Liebigs Ann. Chem. 724 (1969), 214 to 216). The following structural formula I was proposed for bilobalid in a combined publication by the groups of K. Nakanishi et al., R. T. Major et al. and K. Weinges et al. (J. Amer. Chem. Soc. 93 (1971), 3544 to 3546)

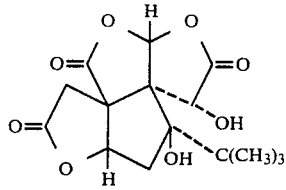

(I)

No medicinal effects of bilobalid have been disclosed. However, it is known that bilobalid has no fungicidal action on *Monilia fructicola* and *Penicillium glaucum* nor any bactericidal action on *Escherichia coli*. Moreover, it is known that bilobalid has no inflammatory action on the mouse ear.

The known extracts prepared from *Ginkgo biloba*, which have been used in medicine since 1965 for the treatment of disturbances of cerebral and peripheral arterial blood flow, contain flavone glycosides as the main constituent. A typical representative of this group is 5,7,3',4'-tetrahydroxyflavono-3-O-α-rhamnopyranosyl-4-O-β-D-(6'''-trans-coumaroyl)glycopyranoside of the formula II

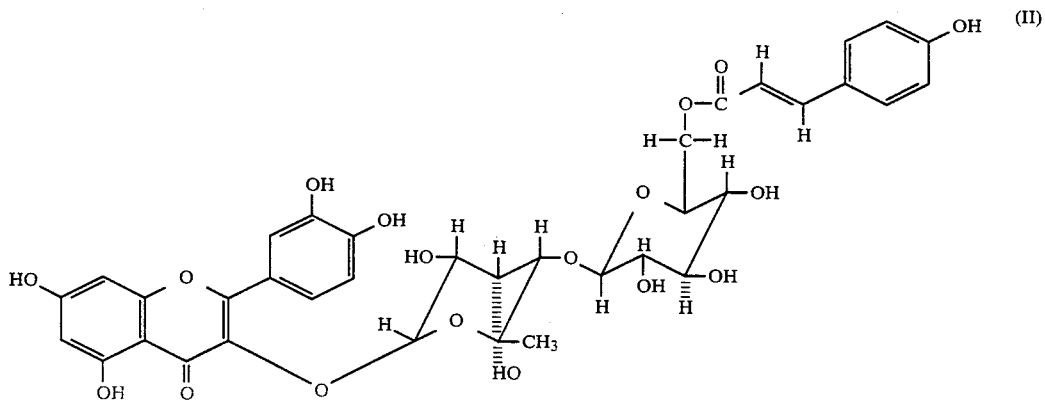

(II)

These extracts, also called monoextracts (see S. S. Chatterjee and G. Trunzler, Ärztezeitschrift für Naturheilverfahren 22 (1981), 593 to 604), can, depending on the mode of their preparation, still contain small amounts of bilobalid and ginkgolides for which, however, to date no therapeutically utilisable biological actions have been disclosed.

Numerous clinical and practical reports which have been published lead to the assumption that, in addition to the therapy of disturbances of blood flow, there are favourable effects on existent neuropathies, neurological and mental functions by monoextracts prepared in a certain manner. To date, these actions have been attributed exclusively to the demonstrated actions of the monoextract in promoting blood flow. However, pharmacological investigations have shown that the monoextract possesses additional properties which go beyond the promotion of blood flow, or vascular, and which might be responsible for the improvements in nervous diseases observed clinically.

SUMMARY OF THE INVENTION

The present invention is based on the surprising finding that bilobalid is suitable for the treatment of certain nervous diseases. Thus, the invention has the object of making available medicaments containing bilobalid for the treatment of nervous diseases.

DETAILED DESCRIPTION OF THE INVENTION

Figure 1:
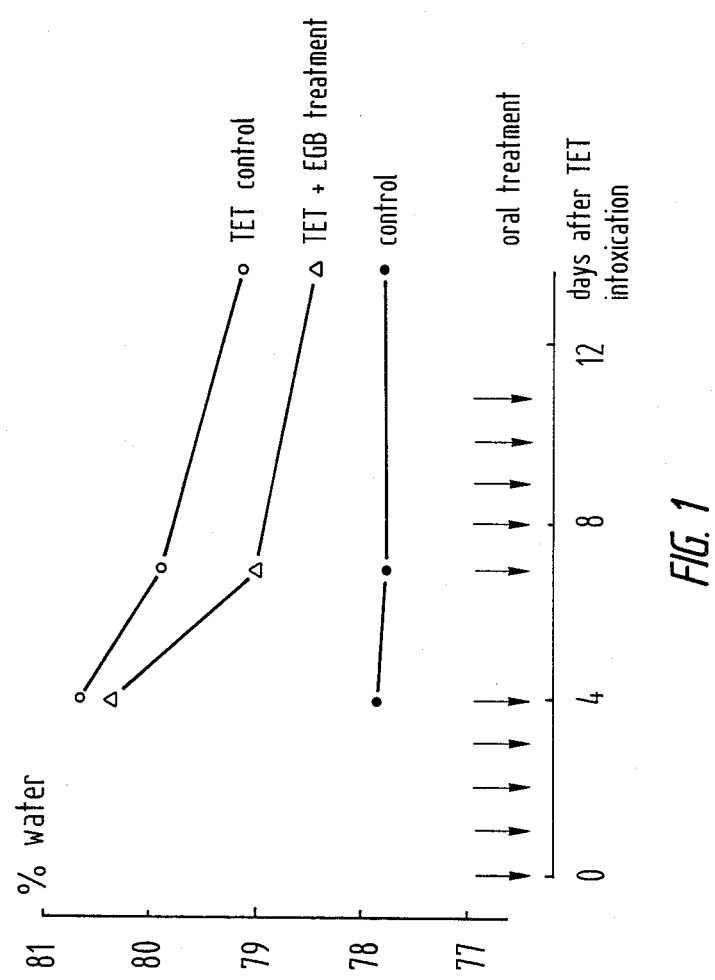

The disorders which can be treated with bilobalid or medicaments containing bilobalid are termed neuropathies, encephalopathies and myelopathies and are associated with at least one of the following symptoms: paraesthesia, paresis, abnormal reflexes, muscular atrophy, muscle spasms, tremor, disturbances of superficial and deep sensibility, headaches and pains in the limbs, disturbances of speech, vision and hearing, vertigo, disturbances of consciousness, lack of coordination and concentration, memory impairment and disorientation. The bilobalid-containing medicaments are suitable for neurological disorders which are caused by or associated with pathological changes in the myelin layer of the nerve fibres.

The great importance of the integrity of the myelin for normal neurological function is generally known. It depends on normal functioning of Schwann's membrane in the peripheral nervous system and the oligodendrocytes in the central nervous system and is, moreover, only ensured when the neurons and axons are intact. Damage to myelin is frequently the consequence of a large number of unconnected pathological states and it is induced by, for example, infections, intoxication, immunological disturbances, genetic defects, tumours, cerebral oedema, trauma and anoxia. Damage to myelin can occur directly or indirectly. Accordingly, a distinction is made between primary and secondary forms. The primary include inflammatory and immunological demyelinating diseases (e.g. multiple sclerosis, post-infectious encephalitis and the Guillain-Barré syndrome), metabolic neuropathies having genetic causes (e.g. the leukodystrophies, the Refsum syndrome and Pelizaeus-Merzbacher disease) and metabolic neuropathies due to toxic effects (e.g. diphtheritic polyneuritis and lead encephalitis). The secondary forms include traumatic neuropathies (e.g. Waller's degeneration), sclerosing neuropathies (e.g. sclerosing panencephalitis), the diabetic, alcohol-related, serogenetic, hereditary and vascular polyneuropathies, and the damage to myelin associated with hemiplegia following apoplexy.

The complex aetiology and pathogenesis of the nervous diseases make it difficult to select pharmacological models suitable for testing potentially effective substances. One possibility is that of testing the therapeutic action of these substances on animals which suffer from neurological signs. It is possible to induce morphological, pathological and electrophysiological signs, resembling the disease, in animals by neurotoxic poisons, such as, for example, organic tin compounds or hexachlorophene[2,2'-methylene-bis(3,4,6-trichlorophenol)]. It is known that, for example, triethyltin chloride brings about an increase in the water content in the brain of various species and induces specific myelopathy in the nerves, and these lead to neuropathies (Int. Rev. Neurobiol, 12 (1970), 45–86). In a similar manner, hexachlorophene produces oedematous damage in the brain of many species, including humans (Arch. Environ. Health, 23 (1971), 114–118; J. Pediatrics, 82 (1973), 976–981) associated with losses and changes in myelin in the nerves (J. Lipid Res., 12 (1971), 570–579; Acta Neuropathol., 53 (1983) 65–74). For this reason, animals treated with this poison are particularly well suited as a model for the disorders mentioned above. Intoxication with triethyltin chloride has been used as a model for myelin damage (Neurochem., 21 (1973), 357–372) and as a model for degenerative disorders of neurological origin (Pharmacol. Biochem. Behavior, 5 (1976), 299–307).

The efficacy of bilobalid has been demonstrated in the following pharmacological models.

EXPERIMENT 1

Male Sprague-Dawley rats (200–300 g body weight) are offered an aqueous solution containing 0.002 percent triethyltin chloride (abbreviated to TET) as drinking liquid for 14 days. Control animals received water. The Gingko biloba monoextract (EGB) and the various test substances are administered orally 1×daily throughout these 14 days. On day 15, the animals are sacrificed, the brain is removed and its water and electrolyte contents are determined. The body weight of the animals during the experiment is checked daily. Treatment with EGB, bilobalid and/or extracts containing bilobalid shows a good protective effect against the decrease in body weight and the increase in the water and $Na^+$ contents in the brain. The results are summarised in Table I.

EXPERIMENT 2

In another experiment, male Sprague-Dawley rats (200–250 g body weight) receive intraperitoneal injections of 20 mg/kg hexachlorophene (suspended in 0.2% agar) for 2 days and only 10 mg/kg on the 3rd day. The test substances are administered orally after administration of hexachlorophene.

TABLE I

| Test substance | | | Mean body weight (g) | | Brain | | | |
|---|---|---|---|---|---|---|---|---|
| | Dose | Drinking liquid | Initial | 14 days | % water | $Na^+$ | $K^+$ | $Na^+/K^+$ |
| | | | | | | mmol/kg dry weight | | |
| Water | | Water | 250 | 320 | 77.90 ± 0.07 | 193.6 ± 0.7 | 442.7 ± 3.9 | 0.44 ± 0.003 |
| Water | | TET 0.002% | 250 | 204 | 80.51 ± 0.19 | 284.4 ± 7.4 | 444.4 ± 3.7 | 0.64 ± 0.020 |
| EGB | 100 mg/kg | TET 0.002% | 238 | 290 | 78.36 ± 0.16 | 189.9 ± 1.7 | 442.2 ± 3.0 | 0.43 ± 0.006 |
| EGB without flavones | 60 mg/kg | TET 0.002% | 242 | 288 | 78.06 ± 0.15 | 186.7 ± 3.1 | 419.1 ± 2.9 | 0.44 ± 0.005 |
| Flavones from EGB | 40 mg/kg | TET 0.002% | 252 | 195 | 80.06 ± 0.27 | 241.3 ± 8.9 | 440.6 ± 3.0 | 0.55 ± 0.02 |
| Bilobalid | 20 mg/kg | TET 0.002% | 288 | 325 | 77.75 ± 0.11 | 187.9 ± 10.4 | 400.6 ± 5.3 | 0.45 ± 0.05 |
| | 10 mg/kg | TET 0.002% | 272 | 318 | 78.16 ± 0.09 | 198.3 ± 2.74 | 452.7 ± 12.9 | 0.44 ± 0.04 |
| | 5 mg/kg | TET 0.002% | 288 | 323 | 78.57 ± 0.19 | 162.6 ± 5.4 | 418.9 ± 14.4 | 0.39 ± 0.020 |
| EGB without flavones and without bilobalid | 60 mg/kg | TET 0.002% | 245 | 210 | 80.29 ± 0.11 | 297.8 ± 6.7 | 429.4 ± 3.3 | 0.69 ± 0.01 |

The control animals receive only 0.2% agar i.p. or tap water orally. On the 4th day, the animals are sacrificed and the water and electrolyte contents in the brain are determined. The body weight of the animals is measured daily throughout the 4 days. As the results in Table II show, treatment with EGB, bilobalid and/or extracts containing bilobalid protects the animals from the development of cerebral oedema and prevents the reduction in body weight.

EXPERIMENT 3

Figure 2:
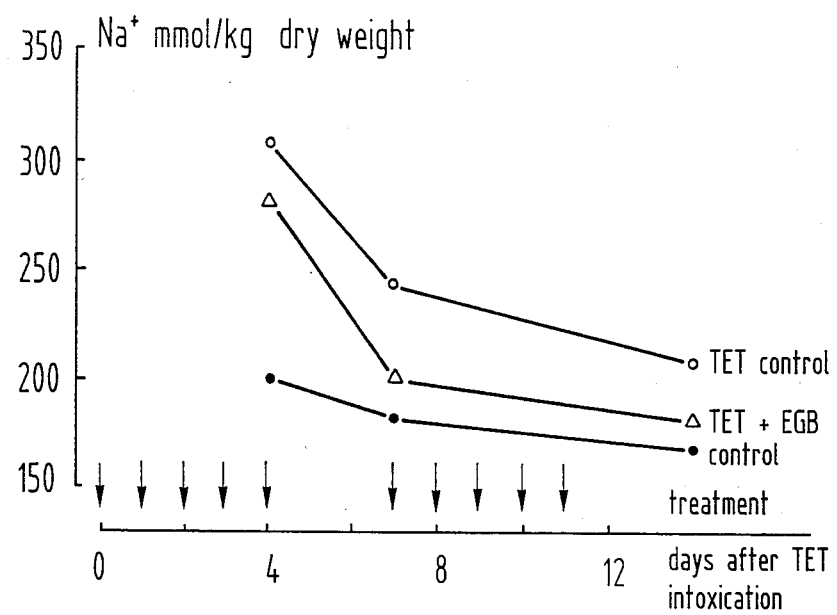
Figure 2:
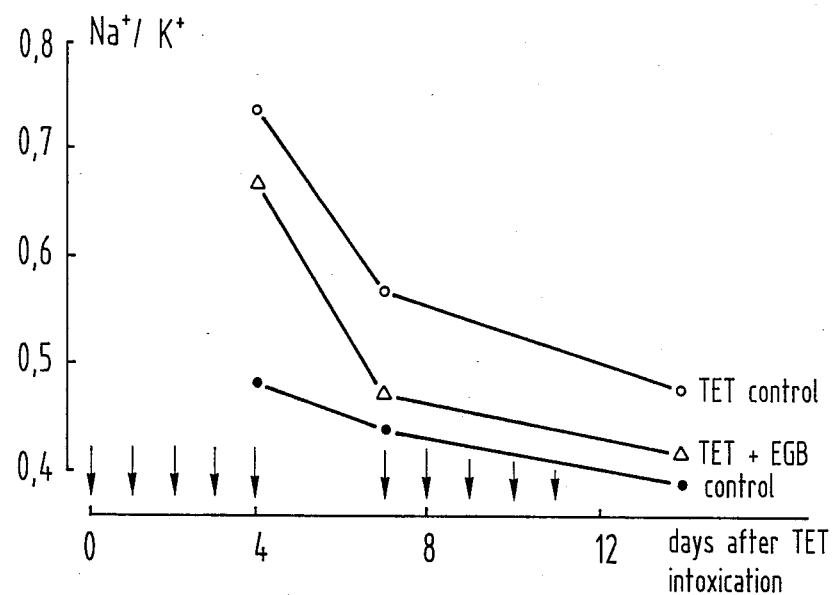

The curative action of EGB is demonstrated in a third experiment. As in Experiment 1, the animals are offered a 0.002 percent triethyltin chloride solution as drinking liquid in place of drinking water for 14 days. The oral treatment with the test substances is started on the 15th day, 1×daily for 5 days a week, with simultaneous replacement of the TET solution by normal tap water. The water and electrolyte contents of the brain are measured at various times after withdrawal of the TET solution and after the start of the treatment. The treatment with EGB brings about a more rapid return of the water and $Na^+$ contents of the brain to normal values and thus shows that it has a good curative action. The results of this experiment are presented in FIGS. 1 and 2.

EXPERIMENT 4

The investigations of the protective action against damage to myelin and its expression as neuropathy is likewise carried out on the triethyltin chloride model. When the animals are treated not for 14 days but for only 6 days with a 0.002 percent TET solution administered in place of the drinking water, they show various signs of neuropathy although no cerebral oedema is detectable in this period. The neuropathy is quantified by measuring the consumption of food and water and by the changes in body weight. In addition, as a specific parameter, the pain reaction time in a hotplate test (at 50° C.) is measured (J. Pharm. Pharmacol., 9 (1957), 381).

that this treatment can eliminate damage to myelin and the signs resulting therefrom.

Rilobalid can be administered in the form of customary medicaments, for example ointments, solutions, coated tablets, tablets, capsules or solutions for injection or infusion, orally or parenterally, for example intramuscularly or intravenously, or topically, for example in the form of plasters acting percutaneously. The dose

TABLE II

| Test substance | | Intraperitoneal treatment | Mean body weight (g) | | Brain | | | |
| --- | --- | --- | --- | --- | --- | --- | --- | --- |
| | Dose | | Initial | 4th day | % water | $Na^+$ | $K^+$ | $Na^+/K^+$ |
| | | | | | | mmol/kg dry weight | | |
| Water | | 0.2% agar | 238 | 266 | 78.50 ± 0.14 | 207.6 ± 4.0 | 433.6 ± 4.1 | 0.48 ± 0.009 |
| Water | | hexachlorophene | 237 | 228 | 80.01 ± 0.19 | 265.4 ± 2.6 | 423.6 ± 2.9 | 0.63 ± 0.02 |
| EGB | 100 mg/kg | hexachlorophene | 245 | 253 | 79.10 ± 0.21 | 240.4 ± 10.9 | 432.3 ± 1.6 | 0.56 ± 0.02 |
| | 50 mg/kg | hexachlorophene | 236 | 243 | 79.40 ± 0.17 | 240.7 ± 13.1 | 421.0 ± 2.6 | 0.57 ± 0.03 |
| | 25 mg/kg | hexachlorophene | 230 | 236 | 79.86 ± 0.12 | 245.9 ± 11.3 | 417.8 ± 2.6 | 0.59 ± 0.02 |
| EGB without flavones | 60 mg/kg | hexachlorophene | 242 | 252 | 78.74 ± 0.24 | 238.2 ± 12.8 | 437.9 ± 2.0 | 0.54 ± 0.03 |
| | 30 mg/kg | hexachlorophene | 230 | 237 | 79.27 ± 0.09 | 227.7 ± 17.2 | 423.4 ± 4.0 | 0.54 ± 0.02 |
| | 15 mg/kg | hexachlorophene | 239 | 240 | 79.55 ± 0.30 | 275.6 ± 10.3 | 422.6 ± 4.9 | 0.65 ± 0.02 |
| Bilobalid | 5 mg/kg | hexachlorophene | 264 | 270 | 77.93 ± 0.17 | 187.9 ± 4.0 | 414.5 ± 4.4 | 0.45 ± 0.01 |
| Flavones from EGB | 40 mg/kg | hexachlorophene | 250 | 240 | 80.51 ± 0.23 | 291.4 ± 20.0 | 432.7 ± 5.4 | 0.67 ± 0.04 |

Oral treatment with EGB or bilobalid carried out throughout these 6 days shows a good protective action against the neuropathic signs, as is clear from Table III.

EXPERIMENT 5

In a simiilar manner, the curative action of bilobalid or extract containing bilobalid is investigated. The animals are offered a 0.002 percent TET solution in place of drinking water for 6 days. Subsequently (from the 7th day), the TET solution is replaced by tap water and, simultaneously, the daily oral treatment is started.

depends on the severity of the disease and the weight of the patient. Coated tablets can be administered after the meals in the morning and evening. The daily doses administered are 5 to 40 mg bilobalid with the normal drug forms, 0.5 to 5 mg bilobalid on parenteral administration, and 5 to 100 mg bilobalid on cutaneous administration.

Bilobalid can be isolated from the leaves of *Ginkgo biloba* by, for example, the method indicated by K. Weinges and W. Bähr, Justus Liebigs Ann. Chem., 724 (1969), 214–216.

TABLE III

| Test substance | | Drinking Liquid | Mean body weight (g) | | Food consumption (g/animal/day) | | Water consumption (ml/animal/day) | | Hotplate reaction time (sec) | |
| --- | --- | --- | --- | --- | --- | --- | --- | --- | --- | --- |
| | Dose | | Initial | Final | Initial | Final | Initial | Final | Initial | Final |
| Water | | Water | 245 | 280 | 25.6 | 24.4 | 37.0 | 33.2 | 39.4 ± 3.4 | 18.6 ± 2.1 |
| Water | | TET 0.002% | 240 | 226 | 24.0 | 12.4 | 34.4 | 11.9 | 36.6 ± 4.3 | >60 |
| EGB | 100 mg/kg/day | TET 0.002% | 245 | 257 | 25.9 | 20.2 | 37.2 | 20.7 | 36.9 ± 2.0 | 21.5 ± 3.32 |
| Bilobalid | 10 mg/kg/day | TET 0.002% | 241 | 261 | 24.3 | 22.1 | 35.1 | 21.9 | 28.9 ± 8.3 | 17.9 ± 5.54 |

TABLE IV

| Treatment | | Body weight (g) | | Food consumption (g/animal/day) | | Water Consumption (ml/animal/day) | | Hotplate reaction time (sec) | |
| --- | --- | --- | --- | --- | --- | --- | --- | --- | --- |
| | Dose | After intoxication | After treatment | After intoxication | After treatment | After intoxication | After treatment | After intoxication | After treatment |
| Water | | 229 | 222 | 10.7 | 18.3 | 11.1 | 13 | 88.4 ± 4.7 | >90 |
| EGB | 100 mg/kg | 212 | 260 | 11.4 | 19.7 | 10.8 | 21.7 | 84.4 ± 13 | 32.9 ± 14.9 |
| EGB | 50 mg/kg | 229 | 246 | 14.9 | 18.6 | 11.6 | 22.4 | 82.1 ± 15.5 | 48.2 ± 22.3 |
| Bilobalid | 10 mg/kg | 227 | 232 | 8.9 | 18.6 | 12.7 | 23.1 | 87.36 ± 7.46 | 48.58 ± 18.44 |
| Bilobalid | 5 mg/kg | 236 | 242 | 10.4 | 17.4 | 11.4 | 31.4 | 88.1 ± 5.67 | 61.58 ± 21.86 |

Treatment is continued for 6 days. The measured parameters (body weight, consumption of food and water, hotplate reaction time) are determined on the 6th day before the treatment and on the 14th day after the treatment. The results are summarised in Table IV.

The fact that treatment with EGB containing bilobalid or with bilobalid prevents the occurrence of neurotoxic signs and of cerebral oedema, and that preexistent damage can be made to regress more quickly, show It is possible to use the customary vehicles and additives for the preparation of medicaments containing bilobalid. Examples of customary vehicles are water, physiological saline, alcohols, polyethylene glycols, glycerol esters, gelatin, carbohydrates, such as lactose and starch, magnesium stearate and talc. Examples of customary additives are preservatives, sterilising agents, lubricants, wetting agents and emulsifiers, colorants, masking flavours and aromatic substances. The selection of the vehicles and additives depends on whether the formulations according to the invention are to be administered enterally, parenterally or locally.

1. Tablets containing pure bilobalid

To prepare tablets each weighing 100 mg and containing 5 mg bilobalid, the following are necessary

| | |
|---|---|
| 5 g | bilobalid |
| 58.5 g | lactose |
| 18 g | microcrystalline cellulose |
| 18 g | maize starch |
| 0.5 g | magnesium stearate |

The first four ingredients are mixed, granulated and, after addition of magnesium stearate, compressed to form tablets in a tabletting machine.

2. Tablets which contain ginkgo extract containing bilobalid

The following recipe results when an extract of ginkgo enriched in bilobalid is used:

| | |
|---|---|
| n g | ginkgo extract, corresponding to 5 mg bilobalid |
| (200-n) g | lactose |
| 25 g | microcrystalline cellulose |
| 24 g | maize starch |
| 1 g | magnesium stearate |

The first four ingredients are mixed, granulated and, after addition of magnesium stearate, compressed in a tabletting machine to give tablets each weighing 250 mg.

3. Capsules

| | |
|---|---|
| 7 g | bilobalid |
| 75 g | lactose |
| 20 g | maize starch |

The ingredients are mixed homogeneously and processed in a customary manner to give capsules containing 100 mg.

4. Injection ampoules

To prepare injection ampoules each containing 2 ml, which contain 0.5 mg bilobalid, the following are required

| | |
|---|---|
| 0.25 g | bilobalid |
| 9 g | sodium chloride |
| ad 100 g | double-distilled water |

The first two ingredients are dissolved in water with gentle heating and stirring. The solution is sterilised by filtration and dispensed into 2 ml ampoules.

5. Liquid oral drug form

| | |
|---|---|
| 5 g | bilobalid |
| 10 g | aromatic essence |
| 5 g | sodium saccharinate |
| 400 g | ethyl alcohol |
| 580 g | distilled water or deionised water. |

The first three ingredients are dissolved in the mixture of ethanol and water. The resulting solution is dispensed into 100 ml bottles. The single dose is 1 ml.

6. Ointment

| | |
|---|---|
| 0.5 g | bilobalid |
| 30 g | emulsifying cetylstearyl alcohol |
| 35 g | high viscosity paraffin |
| 34.5 g | white vaseline. |

The mixture of cetylstearyl alcohol, white vaseline and high viscosity paraffin is melted. The bilobalid is then stirred in. The dosage is 1 to 10 g of ointment per treatment.

What is claimed is:

1. A method for the treatment of neuropathic disorders which comprises administering to a patient requiring said treatment bilobalid in an amount sufficient to alleviate the neuropathic disorders.

2. A method according to claim 1 wherein the neuropathic disorder is demyelinating neuropathy, encephalopathy, myelopathy or cerebral oedemas.

3. A method according to claim 1 wherein the amount of bilobalid is from about 0.5 to about 100 mg per kg of patient body weight.

4. A method according to claim 1 wherein the amount of bilobalid is from about 5 to about 40 mg per kg of patient body weight.

* * * * *